(12) United States Patent
Murayama

(10) Patent No.: US 11,122,961 B2
(45) Date of Patent: Sep. 21, 2021

(54) ENDOSCOPE AND OBJECTIVE OPTICAL UNIT FOR ENDOSCOPE

(71) Applicant: OLYMPUS CORPORATION, Tokyo (JP)

(72) Inventor: Masahiko Murayama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 514 days.

(21) Appl. No.: 16/014,066

(22) Filed: Jun. 21, 2018

(65) Prior Publication Data

US 2018/0303320 A1 Oct. 25, 2018

Related U.S. Application Data

(63) Continuation of application No. PCT/JP2016/081726, filed on Oct. 26, 2016.

(30) Foreign Application Priority Data

Dec. 25, 2015 (JP) .............................. JP2015-254255

(51) Int. Cl.
*A61B 1/00* (2006.01)
*A61B 1/06* (2006.01)
(Continued)

(52) U.S. Cl.
CPC ...... *A61B 1/00096* (2013.01); *A61B 1/00165* (2013.01); *A61B 1/00188* (2013.01);
(Continued)

(58) Field of Classification Search
CPC combination set(s) only.
See application file for complete search history.

(56) References Cited

U.S. PATENT DOCUMENTS 5,235,965 A * 8/1993 Hiroya ................ A61B 1/0008
600/108
5,454,366 A * 10/1995 Ito ....................... A61B 1/0011
600/109

(Continued)

FOREIGN PATENT DOCUMENTS

EP 1481629 A2 12/2004
JP 2002-336190 A 11/2002
(Continued)

OTHER PUBLICATIONS

International Search Report dated Jan. 24, 2017 issued in PCT/JP2016/081726.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope includes: an objective optical unit; an illumination optical system including an illumination lens; and a distal end portion body included in a distal end portion, and the objective lens barrel includes a first lens barrel and a second lens barrel, the first lens barrel includes a disposition hole, an inward projection portion and an outward projection portion, the second lens barrel includes a reception hole, a light input surface and a first distal end face are arranged in a same plane by a beveled surface of a beveled portion being in surface contact with a lens positioning surface of the inward projection portion, and the first distal end face and a second distal end face are arranged in a same plane by a first barrel positioning surface being in surface contact with an objective optical unit positioning surface.

11 Claims, 10 Drawing Sheets

(51) Int. Cl.
*A61B 1/07* (2006.01)
*A61B 1/233* (2006.01)

(52) U.S. Cl.
CPC .............. *A61B 1/0607* (2013.01); *A61B 1/07* (2013.01); *A61B 1/233* (2013.01)

(56) References Cited

U.S. PATENT DOCUMENTS

| | | | | | |
|---|---|---|---|---|---|
| 5,711,756 | A * | 1/1998 | Chikama | ............ | A61B 1/00096 600/112 |
| 7,567,284 | B2 * | 7/2009 | Ikemachi | ................. | G02B 7/28 348/335 |
| 7,695,431 | B2 * | 4/2010 | Okada | .................. | G02B 23/243 600/176 |
| 8,360,967 | B2 * | 1/2013 | Yamamoto | ............... | A61B 1/05 600/176 |
| 2002/0128535 | A1 * | 9/2002 | Kikuchi | ............... | A61B 1/0011 600/101 |
| 2008/0080051 | A1 * | 4/2008 | Yamamoto | ............... | A61B 1/05 359/513 |
| 2008/0242935 | A1 * | 10/2008 | Inoue | ................. | A61B 1/00165 600/176 |
| 2012/0029291 | A1 * | 2/2012 | Wallace | ................. | A61B 1/303 600/160 |
| 2013/0137923 | A1 * | 5/2013 | Honda | ............... | A61B 1/00096 600/109 |

FOREIGN PATENT DOCUMENTS

| | | |
|---|---|---|
| JP | 2005-013708 A | 1/2005 |
| JP | 3854946 B2 | 12/2006 |
| JP | 3958597 B2 | 8/2007 |

* cited by examiner

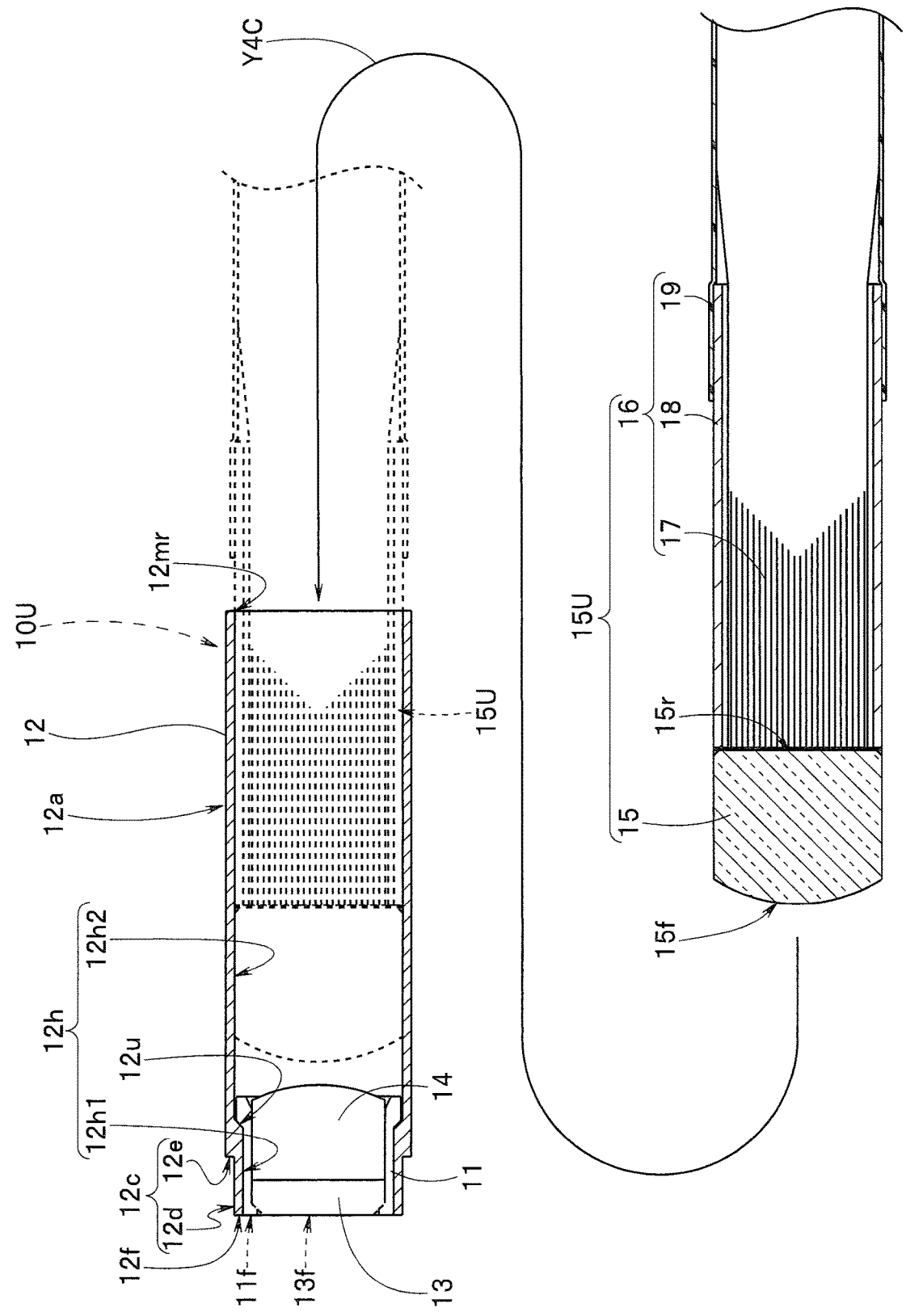

ENDOSCOPE AND OBJECTIVE OPTICAL UNIT FOR ENDOSCOPE

CROSS REFERENCE TO RELATED APPLICATION

This application is a continuation application of PCT/JP2016/081726 filed on Oct. 26, 2016 and claims benefit of Japanese Application No. 2015-254255 filed in Japan on Dec. 25, 2015, the entire contents of which are incorporated herein by this reference.

BACKGROUND OF THE INVENTION

1. Field of the Invention

The present invention relates to an endoscope including a distal end optical lens at a center of a distal end face of a distal end portion of an insertion portion, an illumination lens being disposed on the outer circumferential side of the distal end optical lens, and an objective optical unit for endoscope.

2. Description of the Related Art

In recent years, endoscopes have been used in, e.g., the medical field and the industrial field. The endoscopes include video scopes each including an image pickup apparatus incorporated in a distal end portion of an insertion portion, and fiber scopes each including an image guide obtained by bundling optical fibers, the image guide being inserted inside an insertion portion.

In order to be less invasive for patients, the endoscopes face a demand for thinning of insertion portions. Then, a thin insertion portion can be provided by downsizing, e.g., respective parts such as a distal end optical lens, an illumination lens and a lens barrel.

Japanese Patent No. 3854946 discloses a urological endoscope that enhances insertion capability and reduction of patients' pain. Then, in the urological endoscope, a technique that facilitates of optical adjustment work, prevents yield decrease due to erroneous assembly to an endoscope body, enhances productivity and assemblability enhancement owing to facilitation of positioning and assembling.

SUMMARY OF THE INVENTION

An endoscope according to an aspect of the present invention includes: an objective optical unit arranged on a distal end side, the objective optical unit including a plurality of optical lenses including a distal end optical lens including a beveled portion at a periphery of a light input surface, and an objective lens barrel in which the plurality of optical lenses are fixedly provided; an illumination optical system including an illumination lens arranged on an outer circumferential side of the objective optical unit; and a distal end portion body included in a distal end portion of an insertion portion of the endoscope, the distal end portion body having a cylindrical shape and including a reception space in which the illumination optical system and the objective optical unit are disposed, and the objective lens barrel in the objective optical unit includes a first lens barrel and a second lens barrel, the first lens barrel includes a disposition hole in which the distal end optical lens is disposed, an inward projection portion that protrudes inward from an inner circumferential face of the disposition hole, the inward projection portion including a lens positioning surface with which a beveled surface of the beveled portion of the distal end optical lens is in surface contact, and an outward projection portion provided on a proximal end side of an outer circumferential face of the first lens barrel, the outward projection portion protruding in a predetermined amount outward from the outer circumferential face of the first lens barrel, the second lens barrel includes a reception hole including a first hole in which the outer circumferential face of the first lens barrel is arranged and a second hole in which the outward projection portion is arranged, the second hole having an inner diameter that is larger than an inner diameter of the first hole, in a state in which the beveled surface of the distal end optical lens is in surface contact with the lens positioning surface of the inward projection portion, a light input surface of the distal end optical lens is arranged so as to be in a same plane with a distal end face of the first lens barrel or protrude relative to the distal end face of the first lens barrel, and in a state in which a distal end-side face of the outward projection portion is in surface contact with a level difference surface formed in a level difference portion between an inner face of the first hole and an inner face of the second hole in the reception hole of the second lens barrel, the distal end face of the first lens barrel is arranged so as to be in a same plane with a distal end face of the second lens barrel or protrude relative to the distal end face of the second lens barrel.

An objective optical unit for endoscope according to an aspect of the present invention includes: a distal end optical lens including a beveled surface at an outer circumference; a first lens barrel including a disposition hole in which the distal end optical lens is disposed, an inward projection portion that protrudes inward from an inner circumferential face of the disposition hole, the inward projection portion including a lens positioning surface with which the beveled surface of the distal end optical lens is in surface contact, and an outward projection portion provided on a proximal end side of an outer circumferential face of the first lens barrel, the outward projection portion protruding in a predetermined amount outward from the outer circumferential face of the first lens barrel; a second lens barrel including a reception hole including a first hole in which the outer circumferential face of the first lens barrel is arranged and a second hole in which the outward projection portion is arranged, the second hole having an inner diameter that is larger than an inner diameter of the first hole; a distal end face of the first lens barrel arranged so as to be in a same plane with a distal end face of the second lens barrel or protrude relative to the distal end face of the second lens barrel in a state in which a distal end-side face of the outward projection portion is in surface contact with a level difference surface formed in a level difference portion between an inner face of the first hole and an inner face of the second hole in the reception hole of the second lens barrel; and a light input surface of the distal end optical lens arranged so as to be in a same plane with the distal end face of the first lens barrel or protrude relative to the distal end face of the first lens barrel in a state in which the beveled surface of the distal end optical lens is in surface contact with the lens positioning surface of the inward projection portion.

An endoscope according to another aspect of the present invention includes an objective optical unit including: a distal end optical lens including a beveled surface at an outer circumference; a first lens barrel including a disposition hole in which the distal end optical lens is disposed, an inward projection portion that protrudes inward from an inner circumferential face of the disposition hole, the inward projection portion including a lens positioning surface with which the beveled surface of the distal end optical lens is in surface contact, and an outward projection portion provided on a proximal end side of an outer circumferential face of the first lens barrel, the outward projection portion protruding in a predetermined amount outward from the outer circumferential face of the first lens barrel; a second lens barrel including a reception hole including a first hole in which the outer circumferential face of the first lens barrel is arranged and a second hole in which the outward projection portion is arranged, the second hole having an inner diameter that is larger than an inner diameter of the first hole; a distal end face of the first lens barrel arranged so as to be in a same plane with a distal end face of the second lens barrel or protrude relative to the distal end face of the second lens barrel in a state in which a distal end-side face of the outward projection portion is in surface contact with a level difference surface faulted in a level difference portion between an inner face of the first hole and an inner face of the second hole in the reception hole of the second lens barrel; and a light input surface of the distal end optical lens arranged so as to be in a same plane with the distal end face of the first lens barrel or protrude relative to the distal end face of the first lens barrel in a state in which the beveled surface of the distal end optical lens is in surface contact with the lens positioning surface of the inward projection portion.

An objective optical unit for endoscope according to an aspect of the present invention includes: a distal end optical lens including a beveled surface at an outer circumference; a first lens barrel including a disposition hole in which the distal end optical lens is disposed, an inward projection portion that protrudes inward from an inner circumferential face of the disposition hole, the inward projection portion including a lens positioning surface with which the beveled surface of the distal end optical lens is in surface contact, and an outward projection portion provided on a proximal end side of an outer circumferential face of the first lens barrel, the outward projection portion protruding in a predetermined amount outward from the outer circumferential face of the first lens barrel; and a second lens barrel including a reception hole including a first hole in which the outer circumferential face of the first lens barrel is arranged and a second hole in which the outward projection portion is arranged, the second hole having an inner diameter that is larger than an inner diameter of the first hole.

An endoscope according to another aspect of the present invention includes objective optical unit including: a distal end optical lens including a beveled surface at an outer circumference; a first lens barrel including a disposition hole in which the distal end optical lens is disposed, an inward projection portion that protrudes inward from an inner circumferential face of the disposition hole, the inward projection portion including a lens positioning surface with which the beveled surface of the distal end optical lens is in surface contact, and an outward projection portion provided on a proximal end side of an outer circumferential face of the first lens barrel, the outward projection portion protruding in a predetermined amount outward from the outer circumferential face of the first lens barrel; and a second lens barrel including a reception hole including a first hole in which the outer circumferential face of the first lens barrel is arranged and a second hole in which the outward projection portion is arranged, the second hole having an inner diameter that is larger than an inner diameter of the first hole.

BRIEF DESCRIPTION OF THE DRAWINGS

FIG. 4C is a diagram illustrating a transmission optical system and a relationship between the transmission optical system and the second lens barrel in which the objective lens unit is disposed;

DETAILED DESCRIPTION OF THE PREFERRED EMBODIMENTS

Figure 1:
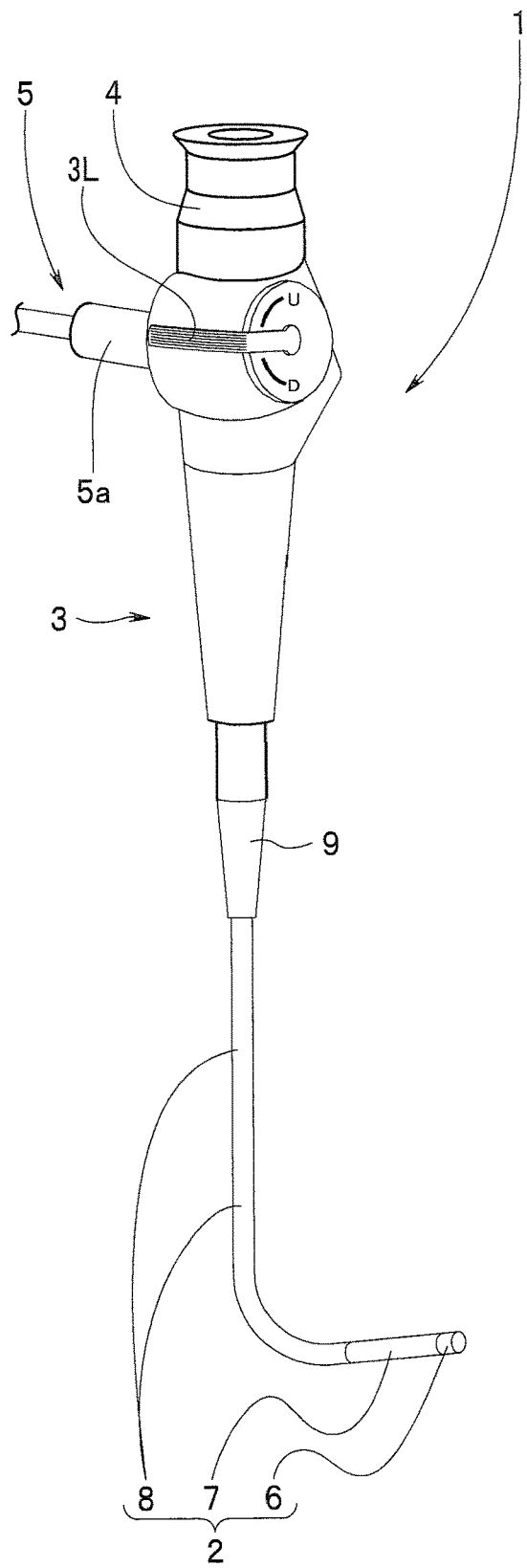
FIG. 1 is a diagram illustrating an endoscope.

Embodiments of the present invention will be described below with reference to the drawings.

Note that in each of the drawings used for the below description, components may be illustrated on different scales so that the respective components have sizes that are large enough to be recognized in the drawing. The present invention is not limited only to the counts and amounts, and the shapes of the components and the size ratios and the relative positional relationships among the components illustrated in the drawings.

An endoscope 1, which is illustrated in FIG. 1, is, for example, a nasopharyngoscope, and mainly includes an insertion portion 2, an operation portion 3 and an eyepiece portion 4. The eyepiece portion 4 is provided at a proximal end portion of the operation portion 3.

Reference numeral 5 denotes a light guide. The light guide 5 includes a connector 5a, and the connector 5a is attachable/detachable to/from a light guide connection port (not illustrated) provided in a side portion of the operation portion 3.

The insertion portion 2 includes a distal end portion 6, a bending portion 7 and a flexible tube portion 8 continuously provided in this order from the distal end side. The flexible tube portion 8 is a tube body having a predetermined flexibility. The bending portion 7 is configured to bend, for example, upward/downward.

Reference numeral 9 denotes a bend prevention portion and has a predetermined elastic force. The bend prevention portion 9 is provided so as to cover a proximal end portion of the flexible tube portion 8 joined to the distal end side of the operation portion 3. The bend prevention portion 9 prevents buckling of the flexible tube portion 8.

Reference numeral 3L denotes a bending operation lever and is provided at the operation portion 3. The bending operation lever 3L is turnable, and upon being turned, pulls/loosens a bending wire (not illustrated) to bend the bending portion 7, for example, two, upward and downward, directions.

Here, the endoscope 1 is not limited to a nasopharyngoscope but may be any of endoscopes each including a distal end optical lens at a substantial center of a distal end face, at least a part of an illumination lens being arranged along an outer circumferential face of the distal end optical lens, such as an ureterorenoscope and a portable endoscope.

A configuration of the distal end side of the insertion portion 2 of the endoscope 1 will be described with reference to FIGS. 2A to 6.

Figure 2A:
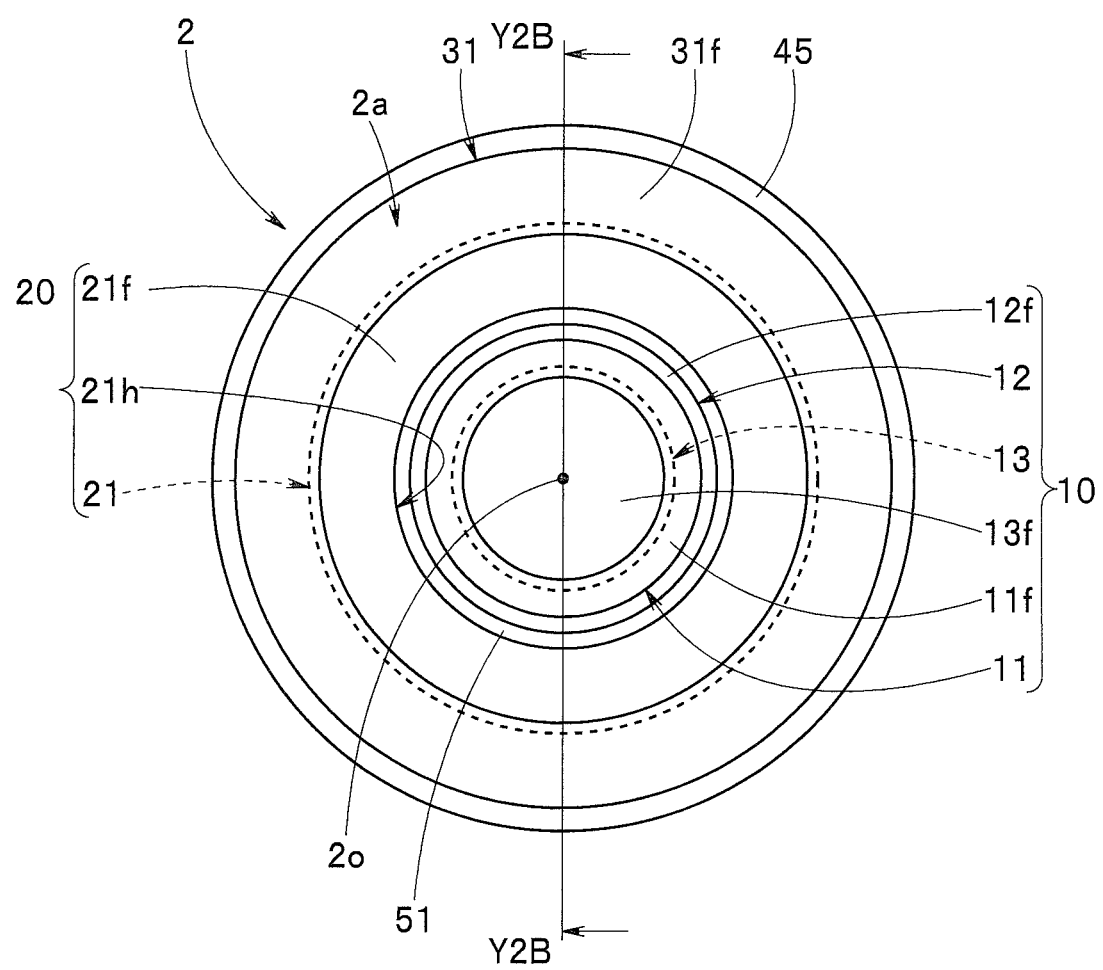
FIG. 2A is a front view illustrating a distal end face of an insertion portion.

As illustrated in FIG. 2A, in a distal end face 2a of the insertion portion 2, e.g., a light input surface 13f of a distal end optical lens 13, an illuminating light output surface 21f of an illumination lens 21, which is an optical member included in an illumination optical system 20 and a distal end portion distal end face 31f of a distal end portion body 31 are provided. The distal end optical lens 13 is an optical member forming a most distal end of a later-described objective optical unit (see reference numeral 10U in FIG. 4C), which is an objective optical system 10.

In the present embodiment, the illumination lens 21 is a ring-shaped lens including a through-hole 21h.

Here, reference numeral 11f denotes a first distal end face, which is a distal end face of a first lens barrel 11 included in the objective optical system 10. Reference numeral 12f denotes a second distal end face, which is a distal end face of a second lens barrel 12 included in the objective optical system 10. Reference numeral 45 denotes a winding and adhesion portion, and reference numeral 51 denotes an adhesion portion.

In the present embodiment, a lens barrel (see reference numeral 10C in FIG. 2B) is configured by the first lens barrel 11 and the second lens barrel 12.

The first lens barrel 11 will be described with reference to FIGS. 3A to 3C.

Figure 3A:
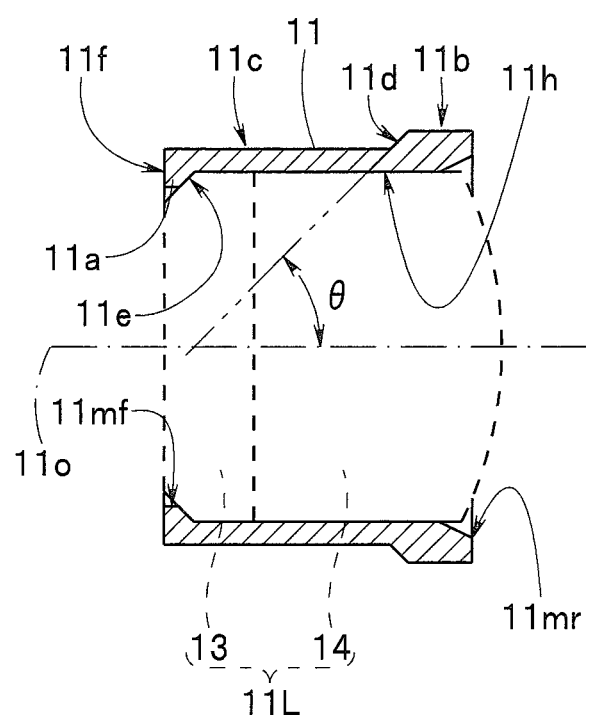
FIG. 3A is a diagram illustrating a first lens barrel.

The first lens barrel 11 illustrated in FIG. 3A is a stepped pipe, for example, a metal pipe made of a stainless steel. In the first lens barrel 11, a disposition hole 11h, which is a straight through-hole, is formed along a first barrel center axis 11o.

Inside the disposition hole 11h, a distal end optical lens 13 and a first optical lens 14 are disposed. The distal end optical lens 13 and the first optical lens 14 configure a compound lens providing a first objective lens (see reference numeral 11L in FIG. 3C) of the objective optical system 10.

In the first lens barrel 11, an inward projection portion 11a and an outward projection portion 11b are provided.

The outward projection portion 11b, which is a thick portion, is a circumferential bump that projects in a predetermined amount outward from an outer circumferential face of a barrel body 11c, which is a thin portion and is located on the barrel proximal end side.

Reference numeral 11d, which is a first barrel positioning surface, is a distal end-side face of the outward projection portion 11b. The first barrel positioning surface 11d is an inclined surface that is at an acute angle θ to a first barrel center axis 11o is formed at a predetermined position.

The first barrel positioning surface 11d is an abutment surface to be brought into abutment with an objective optical unit positioning surface 12u of the later-described second lens barrel 12.

Here, the first barrel positioning surface 11d is not limited to an inclined surface but may be an orthogonal surface that is at right angle θ of 90 degrees to the first barrel center axis 11o.

The inward projection portion 11a is a circumferential bump that projects in a predetermined amount inward from an inner circumferential face of the disposition hole 11h and is located on the barrel distal end side. In the inward projection portion 11a, a lens positioning surface 11e is formed.

Reference numeral 11mf denotes a first barrel distal end opening, and reference numeral 11mr denotes a first barrel proximal end opening.

Figure 3B:
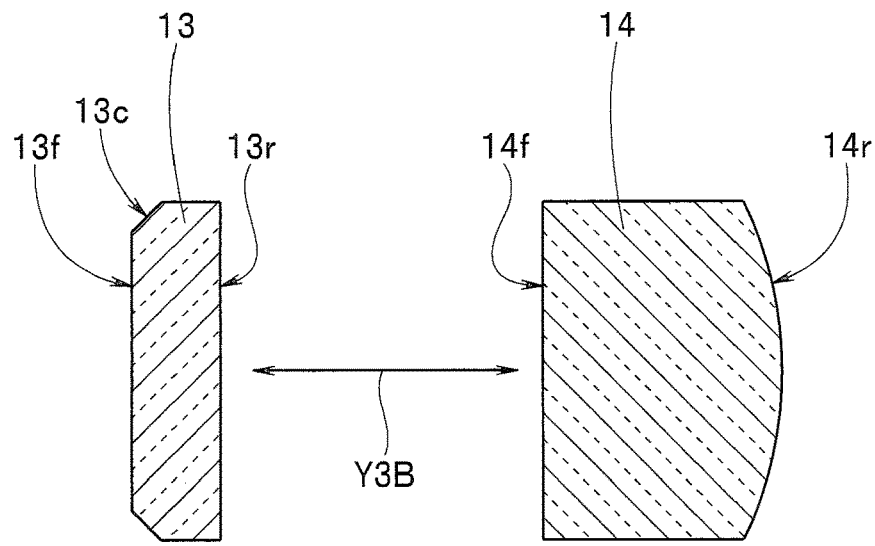
FIG. 3B is a diagram illustrating a distal end optical lens and a first optical lens.

As illustrated in FIG. 3B, the distal end optical lens 13 includes a flat light input surface 13f and a flat light output surface 13r. A beveled portion 13c is formed at a distal end-side periphery of the distal end optical lens 13. In the present embodiment, a beveled surface of the beveled portion 13c is a cut surface, that is, what is called "C (chamfered)-surface".

The first optical lens 14 includes a flat light input surface 14f and a curved light output surface 14r.

An outer diameter of the first optical lens 14 and an outer diameter of the distal end optical lens 13 are set to be equal to each other, and provide a predetermined fit to the disposition hole 11h.

Figure 3C:
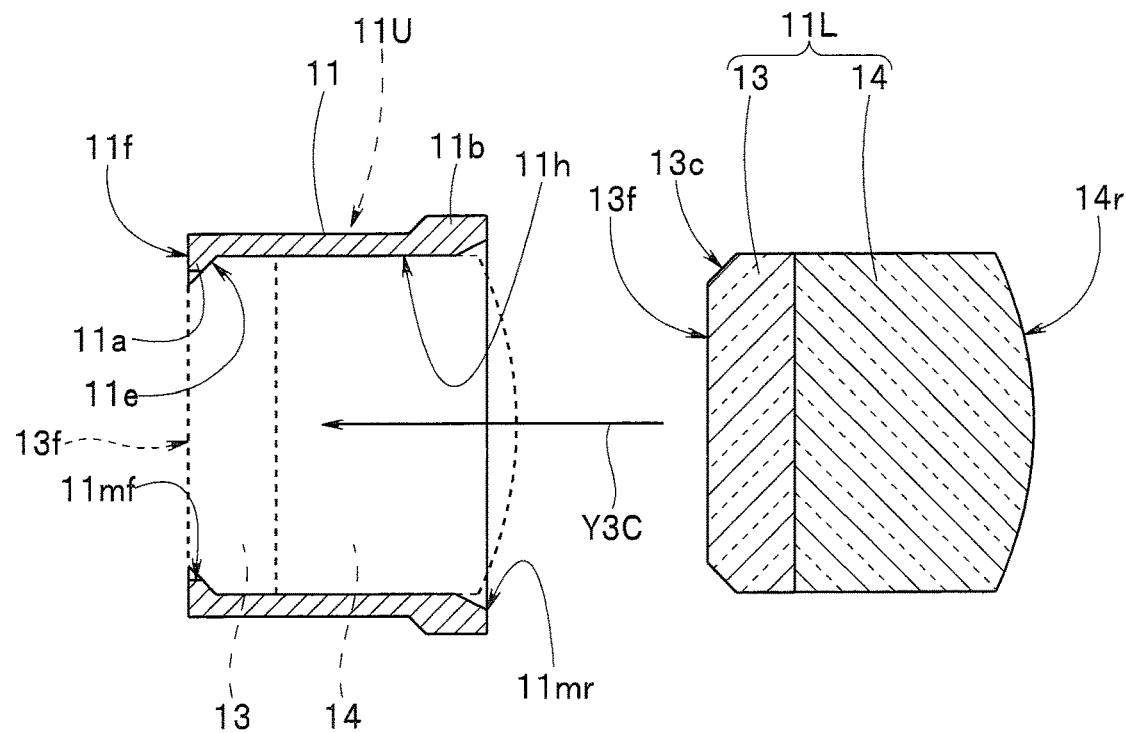
FIG. 3C is a diagram illustrating a relationship between a first objective lens configured by the distal end optical lens and the first optical lens, and the first lens barrel.

As indicated by arrow Y3B in FIG. 3B, the distal end optical lens 13 and the first optical lens 14 configure a first objective lens, which is indicated by reference numeral 11L in FIG. 3C, by putting a light output surface 13r and a light input surface 14f together.

As indicated by arrow Y3C in FIG. 3C, the first objective lens 11L is inserted into the disposition hole 11h from the first barrel proximal end opening 11mr of the first lens barrel 11. The first objective lens 11L is moved toward the inward projection portion 11a, and the distal end optical lens 13 is held without coming off from the first barrel distal end opening 11mf to the outside, by the beveled portion 13c of the distal end optical lens 13 being abutted on the inward projection portion 11a.

In the present embodiment, settings are made so that, in a lens arrangement state in which the beveled surface of the beveled portion 13c is in surface contact with the lens positioning surface 11e of the inward projection portion 11a, the light input surface 13f of the distal end optical lens 13 and the first distal end face 11f of the first lens barrel 11 are arranged in a same plane or although the illustration is omitted, arranged in such a manner that the light input surface 13f protrudes relative to the first distal end face 11f.

In this arrangement state, an adhesive is applied to the first barrel proximal end opening 11mr on the proximal end side of the light output surface 14r to bond and fix the first objective lens 11L to the disposition hole 11h.

As a result, an objective lens unit 11U in which the distal end optical lens 13 and the first optical lens 14 are provided in the first lens barrel 11 is formed. Then, the objective lens unit 11U is supplied as one of components configuring the insertion portion 2.

As described above, the light input surface 13f and the beveled portion 13c are provided on the distal end side of the distal end optical lens 13, and the inward projection portion 11a including the lens positioning surface 11e is provided on the barrel distal end side of the straight disposition hole 11h of the first lens barrel 11.

As a result, when the first objective lens 11L in which the distal end optical lens 13 and the first optical lens 14 are integrated with each other is arranged inside the disposition hole 11h, the first objective lens 11L can reliably be prevented from coming off from the first barrel distal end opening 11mf to the outside.

Therefore, the capability of assembly work of bringing the beveled surface of the beveled portion 13c into close contact with the lens positioning surface 11e of the inward projection portion 11a can substantially be enhanced, and further downsizing of the distal end optical lens 13 and the first lens barrel 11 can be achieved.

Furthermore, in a state in which the beveled surface of the beveled portion 13c is arranged so as to be close contact with the lens positioning surface 11e of the inward projection portion 11a, the light input surface 13f of the distal end optical lens 13 and the first distal end face 11f of the first lens barrel 11 are in the same plane or the light input surface 13f protrudes relative to the first distal end face 11f.

As a result, the disadvantage of the light input surface 13f being blocked by the inward projection portion 11a and the disadvantage of a recess portion including the light input surface 13f as a bottom face being formed on the distal end side of the first lens barrel 11 can be eliminated.

Therefore, a favorable endoscopic image with no vision vignetting can be obtained, and liquid is less likely to remain on the distal end side of the first lens barrel 11, resulting in enhancement in drainage.

Here, although in the present embodiment, one first optical lens 14 is provided, two or more first optical lenses 14 may be provided. The beveled surface is not limited to a C (chamfered)-surface, but may be a curved surface, what is called an R (rounded)-surface. The distal end optical lens 13 may be bonded and fixed to the disposition hole 11h.

Figure 4A:
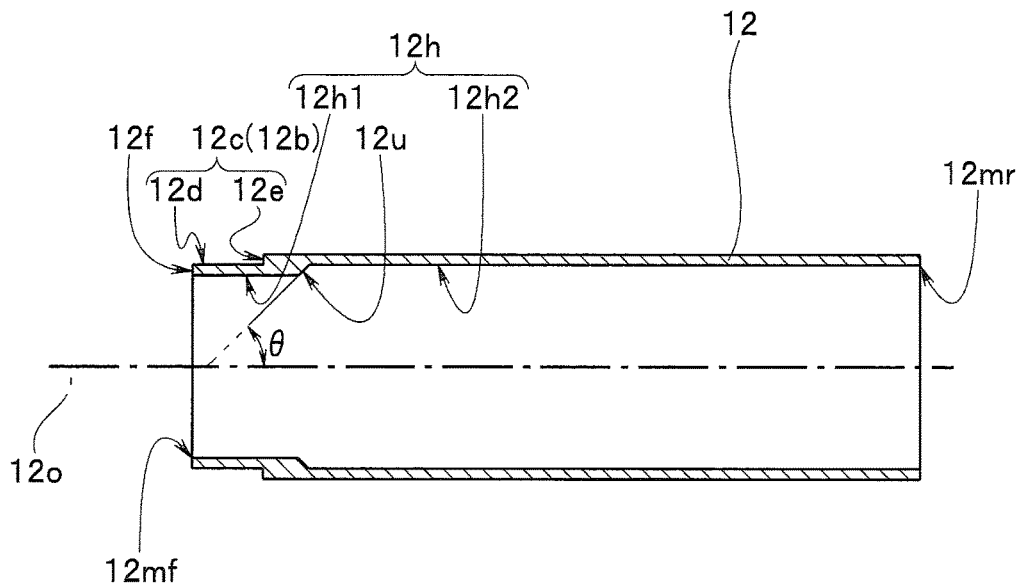
FIG. 4A is a diagram illustrating a second lens barrel.

The second lens barrel 12 illustrated in FIG. 4A is a stepped pipe, for example, a metal pipe made of a stainless steel. In the second lens barrel 12, a reception hole 12h is formed along a second barrel center axis 12o.

The reception hole 12h is a stepped hole including a thin hole and a thick hole. The thin hole, which is a first hole 12h1, is located on the distal end side. The thick hole, which is a second hole 12h2, is located on the proximal end side. Reference numeral 12u denotes an objective optical unit positioning surface, which is an inclined surface that is a level difference surface of a level difference portion between an inner face of the first hole 12h1 and an inner face of the second hole 12h2.

The barrel body 11c of the first lens barrel 11 is arranged inside first hole 12h1. An inner diameter of the first hole 12h1 is larger than an outer diameter of the barrel body 11c and is set to provide a predetermined fit.

The outward projection portion 11b of the first lens barrel 11, and a second objective lens 15 and an image guide distal end sleeve 18, which will be described later, are arranged inside the second hole 12h2. An inner diameter of the second hole 12h2 is larger than each of an outer diameter of the outward projection portion 11b of the first lens barrel 11, an outer diameter of the second objective lens 15 and an outer diameter of the image guide distal end sleeve 18.

Settings are made so that the outward projection portion 11b is arranged so as to provide a loose fit to the second hole 12h2 and the second objective lens 15 and the image guide distal end sleeve 18 are arranged so as to provide a predetermined fit to the second hole 12h2.

In the present embodiment, the objective optical unit positioning surface 12u is a surface inclined at an angle θ, and is formed at an angle that is the same as the angle of the first barrel positioning surface 11d so that the objective optical unit positioning surface 12u is arranged in surface contact with the first barrel positioning surface 11d formed in the outward projection portion 11b of the first lens barrel 11.

Here, reference numeral 12mf denotes a second barrel distal end opening, and reference numeral 12mr denotes a second barrel proximal end opening.

Figure 4B:
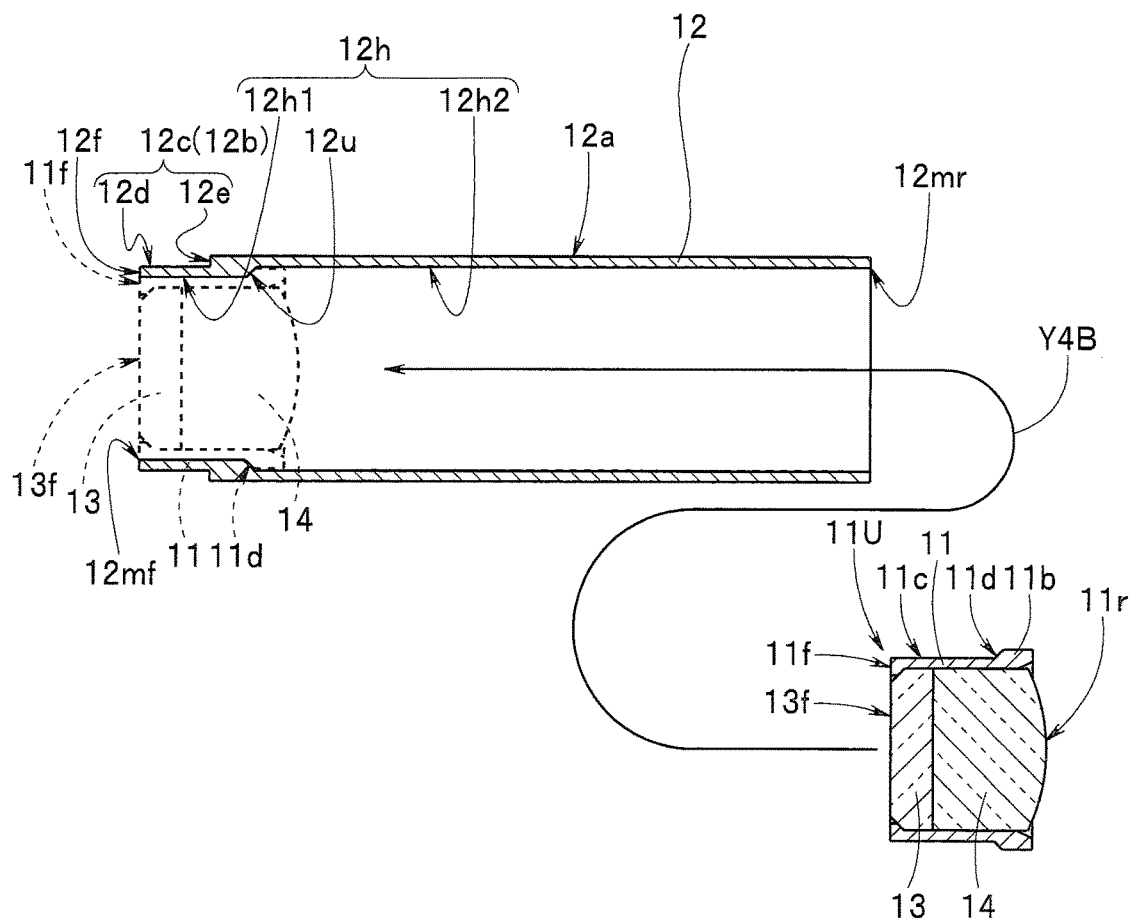
FIG. 4B is a diagram illustrating a relationship between the second lens barrel and an objective lens unit disposed inside the second lens barrel.

As illustrated in FIG. 4B, the objective lens unit 11U is inserted into the second hole 12h2 from the second barrel proximal end opening 12mr of the second lens barrel 12 and moved toward the inside of the first hole 12h1 as indicated by arrow Y4B.

After arrangement of the barrel body 11c of the first lens barrel 11 inside the first hole 12h1, the objective lens unit 11U is held without coming off from the second barrel distal end opening 12mf to the outside, by the first barrel positioning surface 11d of the first lens barrel 11 being abutted on the objective optical unit positioning surface 12u.

In the present embodiment, settings are made so that in a lens unit arrangement state in which the first barrel positioning surface 11d is in close contact with the objective optical unit positioning surface 12u, the first distal end face 11f of the first lens barrel 11 and the second distal end face 12f of the second lens barrel 12 are arranged in a same plane or although the illustration is omitted, the first distal end face 11f protrudes relative to the second distal end face 12f. The first lens barrel 11 and the second lens barrel 12 are integrally fixed via an adhesive in the lens unit arrangement state.

As illustrated in FIG. 4C, inside the second hole 12h2 in which the objective lens unit 11U is disposed, an image pickup unit 15U is disposed as indicated by arrow Y4C.

The image pickup unit 15U, which is one of the components configuring the insertion portion 2, is configured by integration of the second objective lens 15 and the transmission optical system 16. The second objective lens 15, which is a second optical lens, includes a curved light input surface 15f and a flat light output surface 15r.

The transmission optical system 16 mainly includes an image guide fiber bundle 17 configured by bundling optical fibers, an image guide distal end sleeve 18 made of a metal, and a protection tube 19 made of a flexible resin.

The image guide distal end sleeve 18 covers a distal end portion of the image guide fiber bundle 17. The protection tube 19, which is a protection member configured to protect the image guide fiber bundle 17, covers a proximal end portion of the image guide distal end sleeve 18 and a part of the image guide fiber bundle 17, the part extending out from the sleeve 18.

A distal end face of the image guide fiber bundle 17 and a distal end face of the image guide distal end sleeve 18 are bonded and fixed to the light output surface 15r of the second objective lens 15 via a transparent adhesive. An outer diameter of the second objective lens 15 and an outer diameter of the image guide distal end sleeve 18 are set to be substantially equal to each other, and provide a predetermined fit to the second hole 12h2.

The outer diameter of the image guide distal end sleeve 18 is slightly smaller than the outer diameter of the second objective lens 15.

The image pickup unit 15U is inserted into the second hole 12h2 from the second barrel proximal end opening 12mr of the second lens barrel 12 as indicated by arrow Y4C. Subsequently, after focus adjustment by adjustment of a position at which the image pickup unit 15U is arranged, the image pickup unit 15U is fixed integrally to the second lens barrel 12 via an adhesive. As a result, the objective optical unit 10U is configured.

Here, a proximal end portion of the image guide fiber bundle 17 extends to the inside of the operation portion 3 through the inside of the insertion portion 2. A proximal end face of the image guide fiber bundle 17 is arranged so as to face an eyepiece lens (not illustrated) of the eyepiece portion 4.

As illustrated in, e.g., FIG. 4A, a cut-out portion 12c is provided on the distal end side of the second lens barrel 12. The cut-out portion 12c forms a thin barrel portion 12b that is predetermined-dimension thinner than a thick barrel portion 12a configuring a proximal end portion of the second lens barrel 12.

The cut-out portion 12c includes a circumferential face 12d and a bottom face 12e. The bottom face 12e is a level difference surface between the thick barrel portion 12a and the thin barrel portion. The level difference surface is orthogonal to the second barrel center axis 12o.

The bottom face 12e is a holding surface configured to hold the illumination lens 21, and a part of the illuminating light input surface 21r is arranged over an entire circumference of the bottom face 12e.

The circumferential face 12d is an outer circumferential face of the cut-out portion 12c. On the circumferential face 12d, an inner circumferential face of the through-hole 21h of the illumination lens 21 is arranged so as to face the circumferential face 12d.

Figure 5A:
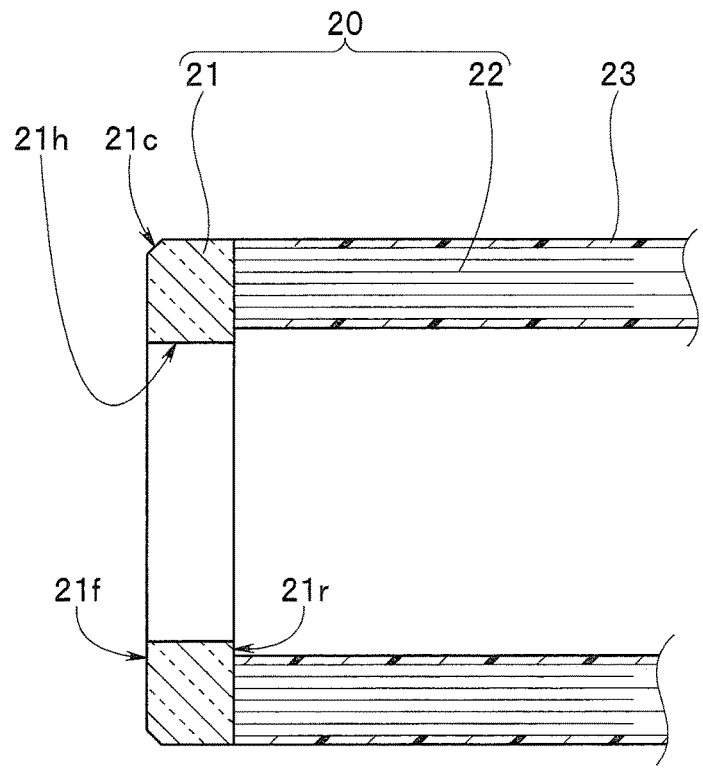
FIG. 5A is a diagram illustrating an illumination optical system.

As illustrated in FIG. 5A, the illumination optical system 20 includes the illumination lens 21 and a light guide fiber bundle 22. The illumination lens 21 is a ring-shaped glass lens including the aforementioned through-hole 21h. The illumination lens 21 includes a flat illuminating light input surface 21r and a flat illuminating light output surface 21f.

A beveled portion 21c is formed at a periphery portion on the illuminating light output surface 21f side of the illumination lens 21. The beveled portion 21c is a cut plane, that is, what is called "C-plane". A distal end face of the light guide fiber bundle 22 is bonded and fixed to the illuminating light input surface 21r of the illumination lens 21 by a transparent adhesive.

Figure 5B:
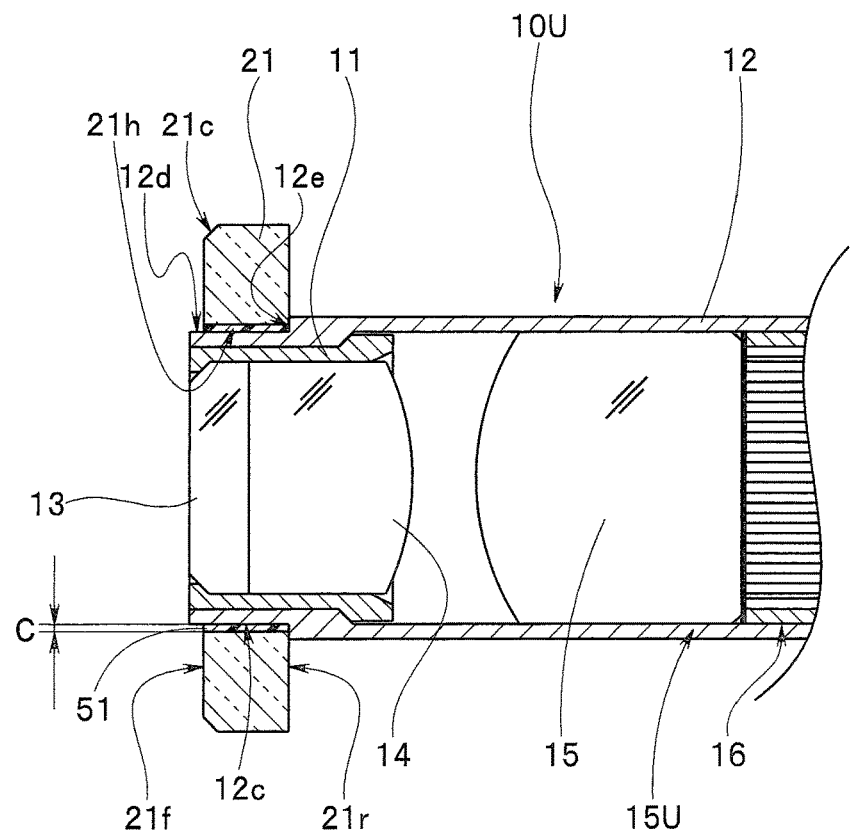
FIG. 5B is a diagram illustrating a relationship between an illumination lens, and a cut-out portion provided in the second lens barrel.

As illustrated in FIG. 5B, the illumination lens 21 is arranged on the cut-out portion 12c.

More specifically, the cut-out portion 12c of the second lens barrel 12 is arranged inside the through-hole 21h of the illumination lens 21.

In this arrangement state, the illuminating light input surface 21r is arranged in contact with the bottom face 12e. The inner circumferential face of the through-hole 21h is arranged so as to face the circumferential face 12d in a spaced manner, and thus a gap C is formed between the inner circumferential face of the through-hole 21h and the circumferential face 12d.

In other words, an outer diameter of the circumferential face 12d is set to be predetermined-dimension smaller than an inner diameter of the through-hole 21h of the illumination lens 21.

An opaque adhesive is charged into the gap C. The adhesive charged in the gap C forms an adhesion section 51 configured to fix the illumination lens 21 integrally to the cut-out portion 12c. The adhesion section 51 doubles as a light-shielding section configured to prevent illuminating light transmitted via the light guide fiber bundle 22 from being reflected by the circumferential face 12d.

Reference numeral 23 in FIG. 5A denotes a protection tube. The protection tube 23 covers and protects the light guide fiber bundle 22. Here, the beveled surface of the beveled portion 21c of the illumination lens 21 is not limited to a C-surface, but may be a curved surface, that is, what is called "R-surface".

Figure 6A:
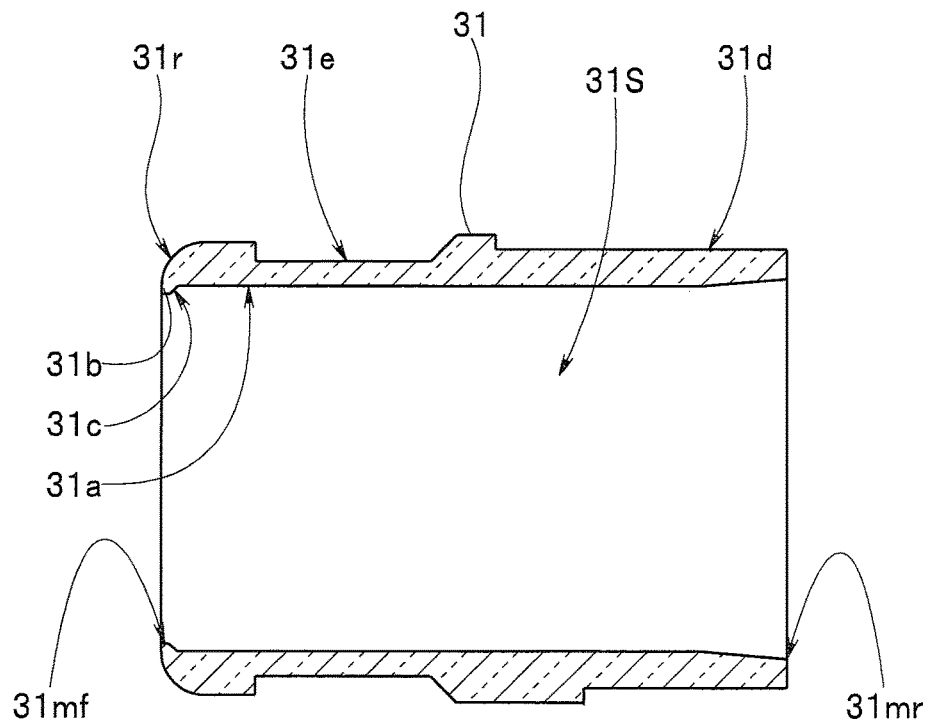
FIG. 6A is a diagram illustrating a distal end portion body.
Figure 6B:
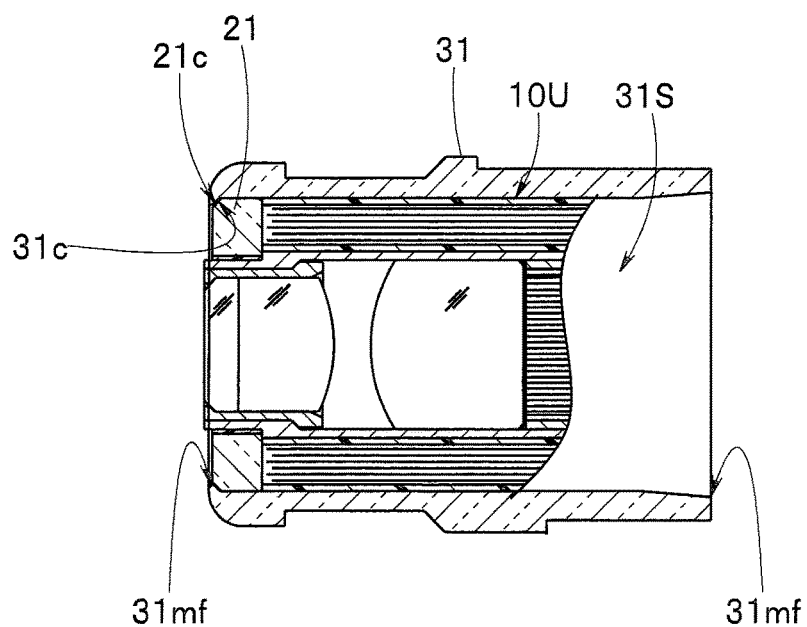
FIG. 6B is a diagram illustrating a relationship between the distal end portion body and the illumination optical system.

The distal end portion body 31 illustrated in FIG. 6A has a cylindrical shape and is included in the distal end portion 6 of the insertion portion 2. The distal end portion body 31 is made of, for example, polysulfone, which is a transparent insulating resin member. The distal end portion body 31 is not limited to one made of polysulfone, but may be one made of a transparent resin such as polycarbonate, acrylic or cyclo-olefin polymer.

Reference numeral 31S denotes a housing space. Inside the housing space 31S, the illumination optical system 20 and the objective optical unit 10U described above are housed.

On the distal end side of the housing space 31S, a circumferential bump 31b that protrudes in a predetermined amount inward from an inner circumferential face 31a is provided. A holding surface 31c is formed in the circumferential bump 31b. The beveled surface of the beveled portion 21c of the illumination lens 21 is arranged in close contact with the holding surface 31c.

Reference numeral 31mf denotes a body distal end opening, and reference numeral 31mr denotes a body proximal end opening.

A piece arranging cut-out portion 31d and a bending rubber arranging groove 31e are provided on the outer circumferential face side of the distal end portion body 31.

Figure 2B:
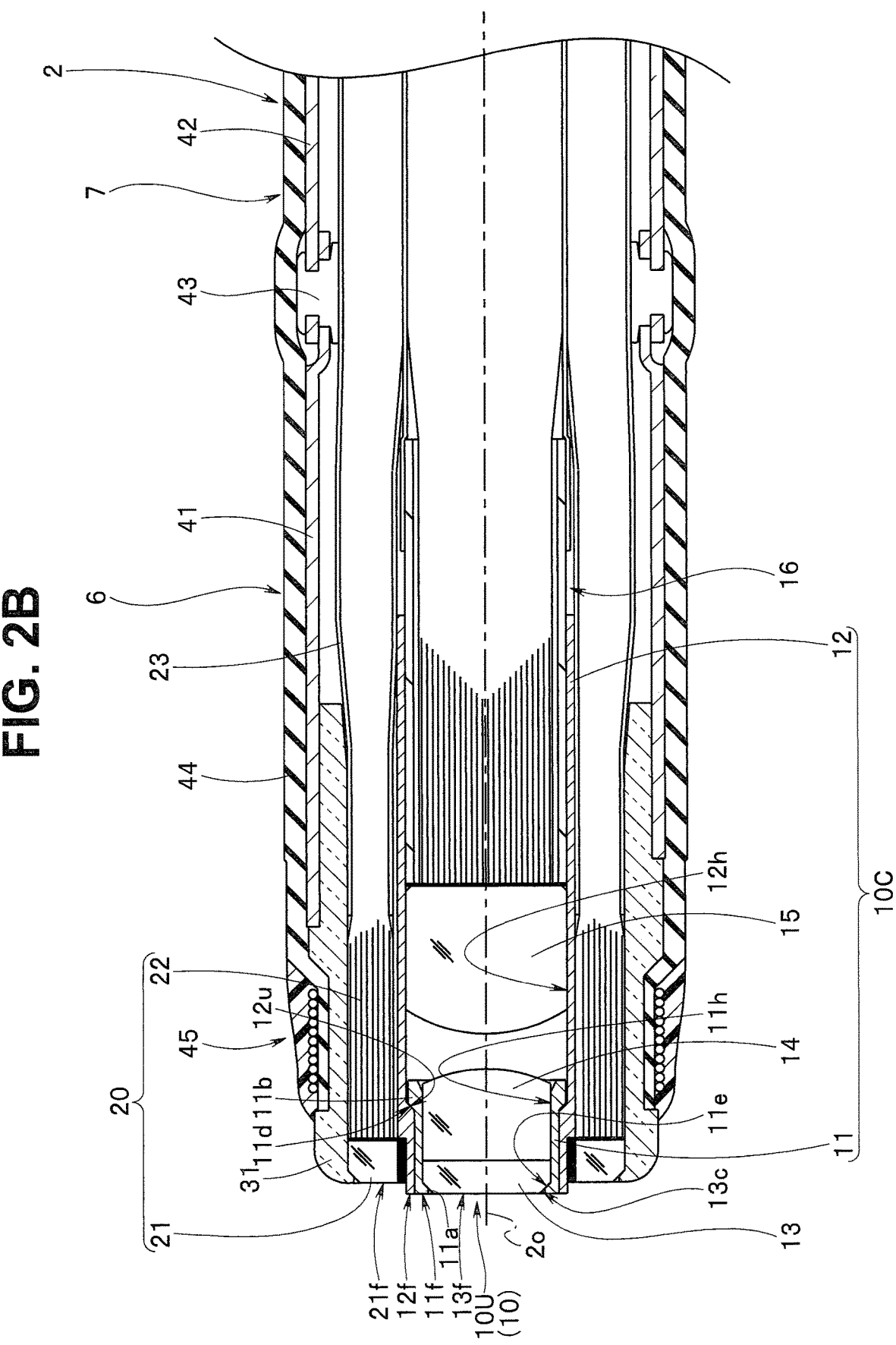
FIG. 2B is a cross-sectional view along the arrow Y2B-Y2B line in FIG. 2A and is a diagram illustrating a configuration of the distal end side of the insertion portion of the endoscope.

The piece arranging cut-out portion 31d is provided on the proximal end side of the distal end portion body 31. A distal end part of a distal end bending piece 41, which is one of bending pieces included in the bending portion 7 illustrated in FIG. 2B, is arranged on the piece arranging cut-out portion 31d. The distal end bending piece 41 is integrally fixed to the distal end portion body 31 via joining or bonding.

The bending rubber arranging groove 31e, which is a circumferential groove, is formed so as to have a predetermined width dimension at a predetermined position in a portion partway of the distal end portion body 31. A distal end part of bending rubber 44 included in the bending portion 7 illustrated in FIG. 2 is arranged in the bending rubber arranging groove 31e. The distal end part of the bending rubber 44 is integrally fixed to the distal end portion body 31 by the winding and adhesion portion 45.

Here, reference numeral 31r denotes an R-surface, which is formed at a distal end-side periphery. The R-surface 31r serves as both a protection surface configured to prevent the wall of nasal cavity from being damaged and an illuminating light output surface. In FIG. 2B, reference numeral 42 denotes an intermediate bending piece. An intermediate bending piece 42 is one of bending pieces included in the bending portion 7, and a plurality of intermediate bending pieces 42 are provided. An intermediate bending piece 42 and the distal end bending piece 41 are turnably joined via a joining pin 43, intermediate bending pieces 42 are turnably joined via respective joining pins 43, an intermediate bending piece 42 and a proximal end bending piece are turnably joined via a joining pin 43.

The objective optical unit 10U is disposed inside the housing space 31S of the distal end portion body 31.

Illumination lens 21 is held without coming off from a body proximal end opening 31mr of the distal end portion body 31 to the outside, by the beveled surface of the beveled portion 21c of the illumination lens 21 being abutted on the holding surface 31c.

Here, the illumination lens 21 is integrally fixed to the distal end portion body 31 via a transparent adhesive.

As a result, illuminating light transmitted via the light guide fiber bundle 22 is outputted from the illuminating light output surface 21f of the illumination lens 21 and is also outputted from the R-surface 31r and an outer circumferential face of the illumination lens 21 through a transparent adhesive layer (not illustrated).

Here, settings are made so that, in a state in which the beveled surface of the beveled portion 21c is in close contact with the holding surface 31c, the illuminating light output surface 21f of the illumination lens 21 and the distal end portion distal end face 31f of the distal end portion body 31 are arranged in a same plane.

The distal end bending piece 41 is fixed to the piece arranging cut-out portion 31d of the distal end portion body 31. In addition, the distal end portion of the bending rubber 44 is arranged in the bending rubber arranging groove 31e and the winding and adhesion portion 45 is provided to integrally fix the distal end portion and the bending rubber arranging groove 31e to each other. Consequently, the insertion portion 2 illustrated in FIG. 2B is configured.

This configuration reliably prevents the illumination lens 21 from coming off from the distal end portion body 31, the objective optical unit 10U from coming off from the through-hole 21h of the illumination lens 21, the objective lens unit 11U from coming off from the second lens barrel 12 of the objective optical unit 10U and the distal end optical lens 13 from coming off from the first lens barrel 11 of the objective lens unit 11U.

As a result, in addition to further downsizing of the distal end optical lens 13 and the first lens barrel 11 described above, the second lens barrel 12, the image pickup unit 15U, the illumination lens 21 and the distal end portion body 31 are downsized, enabling the insertion portion 2 to be thinner.

As a result of the first barrel positioning surface 11d being provided in the first lens barrel 11 included in the objective lens unit 11U and the objective optical unit positioning surface 12u being provided in the second lens barrel 12, the first distal end face 11f of the first lens barrel 11 and the second distal end face 12f of the second lens barrel 12 can easily be arranged in a same plane or the first distal end face 11f of the first lens barrel 11 can be arranged so as to protrude relative to the second distal end face 12f of the second lens barrel 12, by bringing the first barrel positioning surface 11d into close contact with the objective optical unit positioning surface 12u.

As a result, the assemblability can be enhanced while eliminating the disadvantage of a recess portion being formed on each of the distal end side of the first lens barrel 11 and the distal end side of the second lens barrel 12. In other words, the disadvantage of a recess portion being formed on a most distal end face of the insertion portion 2 can be eliminated.

The inner diameter of the through-hole 21h of the illumination lens 21 is set to a predetermined dimension, the cut-out portion 12c arranged inside the through-hole 21h is provided on the distal end side of the second lens barrel 12 included in the objective optical unit 10U, and a part of the illuminating light input surface 21r of the illumination lens 21 is arranged over an entire circumference of the bottom face 12e of the cut-out portion 12c.

As a result, in a state in which the illuminating light input surface 21r of the illumination lens 21 is abutted on the bottom face 12e, a constant gap C can efficiently be provided between the circumferential face 12d and the inner circumferential face of the through-hole 21h.

In the above-described endoscope 1, in order to obtain a favorable endoscopic image with no vision vignetting and cause liquid to be less likely to remain on the distal end face 11f side of the first lens barrel 11, which is the most distal end face of the insertion portion 2, the first lens barrel 11, the second lens barrel 12 and the distal end optical lens 13 of the insertion portion 2 are configured as indicated below.

In the lens arrangement state in which the beveled surface of the beveled portion 13c of the distal end optical lens 13 is in close contact with the lens positioning surface 11e of the first lens barrel 11, the first distal end face 11f of the objective optical unit 10U and the light input surface 13f of the distal end optical lens 13 are arranged in the same plane, and in addition, in the lens unit arrangement state in which the first barrel positioning surface 11d of the objective lens unit 11U is in close contact with the objective optical unit positioning surface 12u of the second lens barrel 12, the second distal end face 12f of the second lens barrel 12, and the first distal end face 11f and the light input surface 13f of the objective optical unit 10U are arranged in a same plane, to eliminate the disadvantage of a recess portion being formed in the most distal end face of the insertion portion 2 and thus prevent liquid from remaining.

Figure 7:
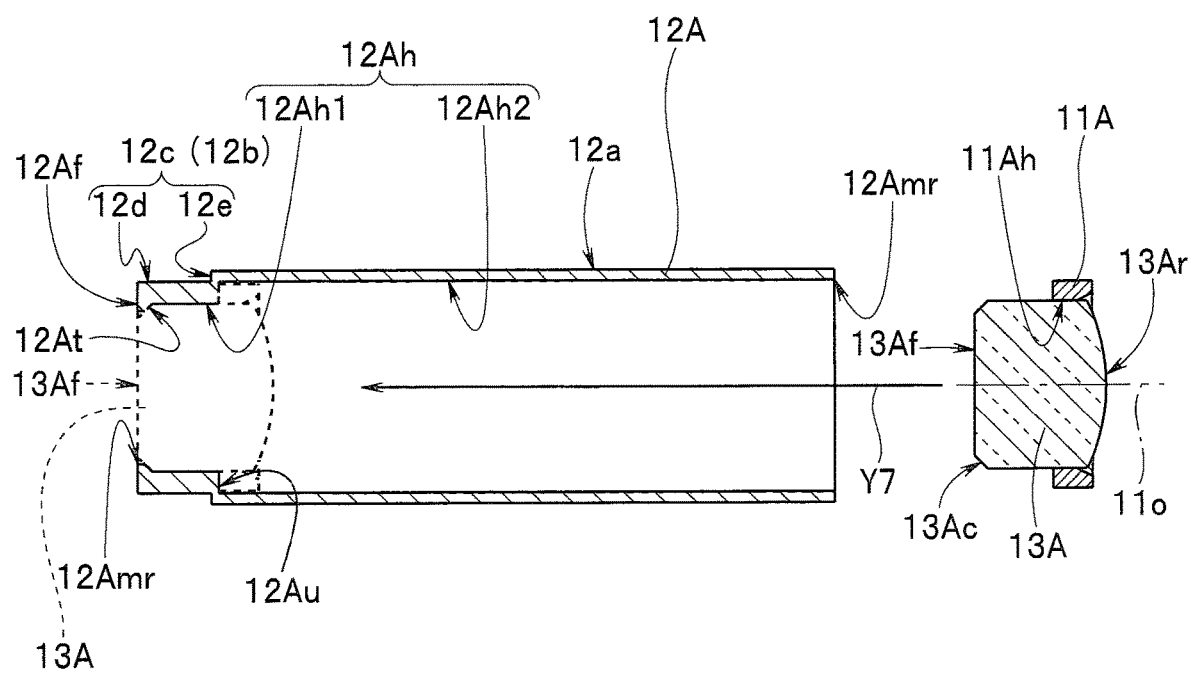
FIG. 7 is a diagram illustrating another example configuration of a first lens barrel, a second lens barrel and a distal end optical lens included in the distal end side of an insertion portion.

However, as illustrated in FIG. 7, a first lens barrel 11A, a second lens barrel 12A and a distal end optical lens 13A may be configured to obtain a favorable endoscopic image with no vision vignetting and eliminate the disadvantage of a recess portion being formed in a most distal end face of an insertion portion 2. Consequently, eliminating the part 11c of the first lens barrel 11 enables the part 12c of the second lens barrel to be thinner and thus enables the distal end portion of the endoscope to be thinner.

In the embodiment illustrated in this figure, a most distal end face of the insertion portion 2 is formed with a second distal end face 12Af of the second lens barrel 12A and a light input surface 13Af of the distal end optical lens 13A.

The first lens barrel 11A is a ring-shaped pipe, for example, a metal pipe made of a stainless steel. In the first lens barrel 11A, a disposition hole 11Ah, which is a straight through-hole, is formed along a first barrel center axis 11o. Opposite end faces of the first lens barrel 11A are flat surfaces orthogonal to the first barrel center axis 11o.

Inside the disposition hole 11Ah, a distal end optical lens 13A, which is a first objective lens, is disposed. The distal end optical lens 13A is a lens obtained by combining the above-described first optical lens 14 with the distal end optical lens 13, and includes a flat light input surface 13Af and a curved light output surface 13Ar. At a periphery on the light input surface 13Af side of the distal end optical lens 13A, a beveled portion 13Ac is formed.

In the present embodiment, a beveled surface of the beveled portion 13Ac is a C-surface. Then, the first lens barrel 11A is integrally fixed at a predetermined position in the distal end optical lens 13A, and configures an objective lens unit 11UA.

On the other hand, the second lens barrel 12A is a stepped pipe that is similar to the above-described second lens barrel 12, and includes a thick barrel portion 12a and a cut-out portion 12c that provides a thin barrel portion 12b. The second lens barrel 12A includes a reception hole 12Ah including a first hole 12Ah1, which is a thin hole, and a second hole 12Ah2, which is a thick hole.

Inside the first hole 12Ah1, the distal end optical lens 13A is arranged. An inner diameter of the first hole 12Ah1 is larger than an outer diameter of the distal end optical lens 13A and is set to provide a predetermined fit.

Inside the second hole 12Ah2, the first lens barrel 11A, and the second objective lens 15 and the image guide distal end sleeve 18 described above are arranged. An inner diameter of the second hole 12h2 is larger than each of an outer diameter of the first lens barrel 11A, the outer diameter of the second objective lens 15 and the outer diameter of the image guide distal end sleeve 18.

The first lens barrel 11A is arranged so as to be loosely fitted in the second hole 12Ah2, and the second objective lens 15 and the image guide distal end sleeve 18 are arranged so as to provide a predetermined fit to the second hole 12Ah2.

Reference numeral 12At denotes an inward projection portion. The inward projection portion 12At protrudes inward from an inner circumferential face of the first hole 12Ah1. The inward projection portion 12At includes a lens positioning surface with which the beveled surface of the beveled portion 13Ac of the distal end optical lens 13A is in surface contact. An objective optical unit positioning surface 12Au is provided in a level difference surface of a level difference portion between an inner face of the first hole 12Ah1 and an inner face of the second hole 12Ah2. The objective optical unit positioning surface 12Au according to the present embodiment is an orthogonal surface and is in close contact with a distal end face of the first lens barrel 11A.

Reference numeral 12Amf denotes a second barrel distal end opening, and reference numeral 12Amr denotes a second barrel proximal end opening.

In the present embodiment, the objective lens unit 11UA is inserted into the second hole 12Ah2 from the second barrel proximal end opening 12Amr of the second lens barrel 12 and moved toward the first hole 12Ah1 as indicated by arrow Y7.

Then, the objective lens unit 11UA is held without coming off from the second barrel distal end opening 12Amf to the outside by the distal end face of the first lens barrel 11A configuring the objective lens unit 11UA being abutted on the objective optical unit positioning surface 12Au, and upon the abutment, the beveled surface of the beveled portion 13Ac of the distal end optical lens 13A comes into close contact with the lens positioning surface of the inward projection portion 12At.

As a result, the light input surface 13Af of the distal end optical lens 13A and the second distal end face 12Af of the second lens barrel 12A are arranged in a same plane, eliminating the disadvantage of a recess portion being formed in a most distal end face of an insertion portion 2.

In this arrangement state, the first lens barrel 11A and the second lens barrel 12A are integrally fixed with an adhesive. The rest of the configuration of the insertion portion 2 is similar to the configuration of the insertion portion 2 in the above-described embodiment.

The present invention is not limited only to the above-described embodiments and various modifications are possible without departing from the spirit of the invention.

The present invention enables provision of an endoscope and an objective optical unit for endoscope, the endoscope and the objective optical unit having a thin insertion portion of the endoscope, preventing vision vignetting and drainage deterioration, facilitating positioning work and assembly work and preventing yield decrease due to, e.g., erroneous assembly and enhancing in productivity.

What is claimed is:

1. An endoscope comprising:
   an objective optical unit arranged on a distal end side, the objective optical unit including a plurality of optical lenses including a distal end optical lens including a beveled portion at a periphery of a light input surface, and an objective lens barrel in which the plurality of optical lenses are fixedly provided;
   an illumination optical system including an illumination lens arranged on an outer circumferential side of the objective optical unit; and
   a distal end portion body included in a distal end portion of an insertion portion of the endoscope, the distal end portion body having a cylindrical shape and including a reception space in which the illumination optical system and the objective optical unit are disposed, wherein:
   the objective lens barrel in the objective optical unit includes a first lens barrel and a second lens barrel;
   the first lens barrel comprises:
     a disposition hole in which the distal end optical lens is disposed,
     an inward projection portion that protrudes inward from an inner circumferential face of the disposition hole, the inward projection portion including a lens positioning surface with which a beveled surface of the beveled portion of the distal end optical lens is in surface contact,
     an outward projection portion provided on a proximal end side of an outer circumferential face of the first lens barrel, the outward projection portion protruding in a predetermined amount outward from the outer circumferential face of the first lens barrel; and
     a first level difference surface that connects the outer circumferential face on a distal end side of the first lens barrel and an outer circumferential face of the outward projection portion;
   the second lens barrel comprises:
     a reception hole including a first hole in which the outer circumferential face on the distal end side of the first lens barrel is arranged and a second hole in which the outward projection portion is arranged, the second hole having an inner diameter that is larger than an inner diameter of the first hole, and
     a second level difference surface that connects an inner face of the first hole and an inner face of the second hole;
   wherein in a state in which the beveled surface of the distal end optical lens is in surface contact with the lens positioning surface of the inward projection portion, the light input surface of the distal end optical lens is arranged so as to be in a same plane with a first distal end face of the first lens barrel; and
   in a state in which the first level difference surface of the first lens barrel is in surface contact with the second level difference surface in the reception hole of the second lens barrel, and the first lens barrel is positioned with respect to the second lens barrel, the first distal end face of the first lens barrel is arranged so as to be in a same plane with a second distal end face of the second lens barrel.

2. The endoscope according to claim 1, wherein:
   the second lens barrel includes a cut-out portion for arranging the illumination lens on a distal end side of the outer circumferential face of the second lens barrel; and the cut-out portion includes a circumferential face that an inner face of the illumination lens faces, and a restricting surface, a part of an illuminating light input surface of the illumination lens being in surface contact with an entire circumference of the restricting surface.

3. The endoscope according to claim 1, wherein:
the illumination lens includes a beveled portion at a periphery of an illuminating light output surface of the illumination lens; and
the distal end portion body includes an illumination optical system positioning surface that protrudes inward from an inner circumferential face of a reception space in which the illumination lens is disposed, the illumination optical system positioning surface being in surface contact with a beveled surface of the beveled portion of the illumination lens, on a distal end side of the reception space.

4. The endoscope according to claim 3, wherein the distal end portion body includes a transparent resin member.

5. The endoscope according to claim 1, wherein the first level difference surface is a positioning surface of the first lens barrel, the positioning surface being arranged in parallel with a direction intersecting a center axis of the first lens barrel.

6. The endoscope according to claim 5, wherein the first level difference surface is an inclined surface having an acute angle with respect to a center axis of the first lens barrel.

7. The endoscope according to claim 5, wherein the first level difference surface is an orthogonal surface that is orthogonal to a center axis of the first lens barrel.

8. The endoscope according to claim 1, wherein the plurality of optical lenses include the distal end optical lens including the beveled portion at the periphery of the light input surface having a flat shape, and
the distal end optical lens is configured such that,
in the state in which the beveled surface of the beveled portion is in surface contact with the lens positioning surface of the inward projection portion, the light input surface having the flat shape is arranged so as to be in a same plane with the first distal end face of the first lens barrel, and
in the state in which the first level difference surface of the first lens barrel is in surface contact with the second level difference surface in the reception hole of the second lens barrel, and the first lens barrel is positioned with respect to the second lens barrel, the light input surface having the flat shape is arranged so as to be in a same plane with the second distal end face of the second lens barrel.

9. The endoscope according to claim 8, wherein in the objective lens barrel of the objective optical unit, the first lens barrel that holds at least the distal end optical lens and the second lens barrel that holds at least one of the plurality of optical lenses are fitted to each other.

10. An objective optical unit for endoscope, the objective optical unit comprising:
a distal end optical lens including a beveled surface at an outer circumference;
a first lens barrel including a disposition hole in which the distal end optical lens is disposed, an inward projection portion that protrudes inward from an inner circumferential face of the disposition hole, the inward projection portion including a lens positioning surface with which the beveled surface of the distal end optical lens is in surface contact, an outward projection portion provided on a proximal end side of an outer circumferential face of the first lens barrel, the outward projection portion protruding in a predetermined amount outward from the outer circumferential face of the first lens barrel, and a first level difference surface that connects the outer circumferential face on a distal end side of the first lens barrel and an outer circumferential face of the outward projection portion;
a second lens barrel including a reception hole including a first hole in which the outer circumferential face on the distal end side of the first lens barrel is arranged and a second hole in which the outward projection portion is arranged, the second hole having an inner diameter that is larger than an inner diameter of the first hole, the second lens barrel including a second level difference surface that connects an inner face of the first hole and an inner face of the second hole;
a distal end face of the first lens barrel arranged so as to be in a same plane with a distal end face of the second lens barrel in a state in which the first level difference surface of the first lens barrel is in surface contact with the second level difference surface of the second lens barrel, and the first lens barrel is positioned with respect to the second lens barrel; and
a light input surface of the distal end optical lens arranged so as to be in a same plane with the distal end face of the first lens barrel in a state in which the beveled surface of the distal end optical lens is in surface contact with the lens positioning surface of the inward projection portion.

11. An endoscope comprising the objective optical unit for endoscope according to claim 10.

* * * * *